(12) United States Patent
Gross et al.

(10) Patent No.: US 8,021,438 B2
(45) Date of Patent: Sep. 20, 2011

(54) CATIONIC ACYLPYRIDINIUM DERIVATIVES FOR USE AS BLEACH ACTIVATORS

(75) Inventors: Wibke Gross, Hueckelhoven (DE); Denise Fuhr, Hamburg (DE); Ralph Nemitz, Juechen (DE); Astrid Kleen, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 13/036,108

(22) Filed: Feb. 28, 2011

(65) Prior Publication Data

US 2011/0146006 A1    Jun. 23, 2011

Related U.S. Application Data

(63) Continuation of application No. PCT/EP2009/057015, filed on Jun. 8, 2009.

(30) Foreign Application Priority Data

Aug. 28, 2008    (DE) .......................... 10 2008 044 715

(51) Int. Cl.
*A61Q 5/10*    (2006.01)

(52) U.S. Cl. .............. 8/405; 8/406; 8/409; 8/435; 8/568

(58) Field of Classification Search .............. 8/405, 406, 8/409, 435, 568
See application file for complete search history.

(56) References Cited

U.S. PATENT DOCUMENTS 6,371,993 B1 *    4/2002    Moeller et al. .................... 8/407

FOREIGN PATENT DOCUMENTS

| | | |
|---|---|---|
| DE | 102006020789 A1 | 11/2007 |
| DE | 102007047685 A1 | 7/2008 |
| EP | 0998908 A2 | 5/2000 |
| EP | 1800655 A1 | 6/2007 |
| EP | 1891927 A2 | 2/2008 |
| EP | 1905418 A2 | 4/2008 |
| WO | 2005115322 A1 | 12/2005 |

OTHER PUBLICATIONS

Stic Search Report dated Apr. 11, 2011.*
Röomp-Lexicon of Chemstry, George Thieme Verlag, 10th Edition, 1997, pp. 1764.
Schrader, Karlheinz. Grundlagen und Rezepturen der Kosmetika (Fundamentals and Formulations of Cosmetics), 2, Hüthig Buch Verlag GmbH, Heidelberg 1989.

* cited by examiner

*Primary Examiner* — Eisa B Elhilo
(74) *Attorney, Agent, or Firm* — David P. LeCroy

(57) ABSTRACT

Agent for dyeing keratin fibers while simultaneously bleaching the keratin fibers. The agent contains, in a cosmetic carrier, at least one oxidation dye precursor and at least one cationic acylpyridinium derivative.

14 Claims, No Drawings

CATIONIC ACYLPYRIDINIUM DERIVATIVES FOR USE AS BLEACH ACTIVATORS

CROSS REFERENCE TO RELATED APPLICATIONS

The present application is a continuation of International Patent Application No. PCT/EP2009/057015 filed 8 Jun. 2009, which claims priority to German Patent Application No. 10 2008 044 715.3 filed 28 Aug. 2008, both of which are incorporated herein by reference.

The present invention relates to an agent for dyeing and simultaneously lightening keratin-containing fibers, especially human hair. The agent contains, in a cosmetic carrier, at least one dyeing compound as well as a cationic derivative of an acylpyridine. The invention further relates to a method for applying such agents on keratin-containing fibers. Moreover, the invention relates to use of the agent for dyeing and simultaneously lightening hair.

Modifying the shape and particularly the color of hair is an important area of modern cosmetics. This allows the appearance of the hair to be adapted to both actual fashion tendencies and the personal preferences of each person. Consumers resort to dyeing agents for fashionable hair style color schemes or for concealing gray or even white hair with fashionable or natural color tints. In addition to the desired coloration power, these agents should cause the least possible damage to hair, and preferably also possess additional care characteristics.

For the provision of dyeing cosmetic agents, especially for skin or keratin-containing fibers such as human hair, one skilled in the art is aware of diverse dyeing systems according to dyeing requirements. If the intent is to lighten or even bleach substrates, the original coloration is removed mostly oxidatively by employing appropriate oxidizing agents, such as hydrogen peroxide.

Dyeing, especially color lightening of dark hair is a key wish of many users. For consumers having strongly pigmented hair, sufficient lightening is a fundamental requirement in the areas of fashion and natural tints for the production of intensive nuances that are lighter than the original hair color. For dark blond, brown or black hair, it is difficult to obtain significant lightening by only using hydrogen peroxide.

Use of a combination of hydrogen peroxide and persulfate salts for boosting the blond-dyeing effect is known from the prior art. Generally, however, these mixtures of oxidizing agents cause both heavy damage to the hair and oxidative destruction of the dyes obtained in the dyeing process from the developer and coupler type dye precursors, preventing simultaneous strong lightening and dyeing from being achieved in this way.

Oxidative hair dyes, especially with an additional blonding effect, are however also beset with additional disadvantages. Firstly, the use of oxidizing agents damages the hair structure and the hair surface. The hair becomes brittle, its elasticity diminishes, and combability decreases. This damage increases with application time. Conventional oxidative dyes typically must act for periods of 30 minutes and more on the hair fibers. An increase in contact time leads to an increased impairment of the hair structure. Secondly, oxidative dyes generally need a basic pH for dyeing, especially from pH 9.0 to pH 10.5. Such high pH values are required in order to ensure that the external squamosal layer (cuticula) opens, thereby enabling the active species (dye precursors and/or hydrogen peroxide) to penetrate into the hair. However, this basic medium represents another factor that damages the hair and its structure, and the damage likewise becomes more significant with increased application times. Moreover, the spreading of the external squamosal layer leads to an unpleasant surface feel of the hair and consequently to a worse combability when wet and when dry. In addition, the basic pH is often adjusted with ammonia as the alkalizing agent, because ammonia-containing dyes possess additional advantages with respect to dyeing power. A dye of this type is disadvantageous for a user in that, in addition to damage to the hair, it can cause irritation to the eyes or scalp, thereby provoking sensitization or even allergic reactions. Moreover, such dyes possess an intensive, unpleasant smell that can also lead to irritation of the nasal mucous membrane. Furthermore, production and storage of ammonia-containing dyeing agents can be problematic regarding handling and stability.

Accordingly, the present invention provides dyes for oxidative dyeing of hair which exhibit a significant blond-dyeing effect and which also can dye hair in intensive and brilliant nuances.

Generally, the dye mixture must remain on the hair for a period of 30 to 45 minutes for permanent hair coloration. For consumers, a shortened contact time strongly simplifies the hair dyeing process and increases the comfort during application. Although reduction in contact time is desirable, technical realization is problematic as short application times likewise result in a weaker lightening of the hair. Accordingly, this invention provides for oxidative dyes with a lightening power that is superior to the prior art and which can shorten contact time. Finally, it is desirable to provide dyeing and shape-changing agents which reduce potential irritation especially due to the addition of ammonia to as low as possible. It has now been surprisingly found that the above listed requirement profile can be met in an excellent manner by adding a combination of oxidation dye precursors and specific bleach activators.

Accordingly, a first subject matter of the invention is an agent for dyeing and simultaneously lightening keratinic fibers comprising in a cosmetic carrier at least one oxidation dye precursor and at least one cationic acylpyridinium derivative according to the following Formula (I),

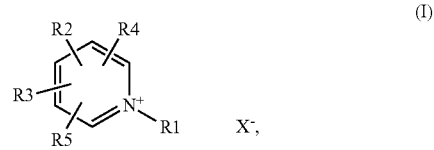

wherein
R1 is a $C_1$-$C_6$ alkyl group, a $C_2$-$C_6$ alkenyl group, a $C_2$-$C_6$ hydroxyalkyl group, a $C_1$-$C_6$ alkoxy $C_2$-$C_6$ alkyl group, a carboxy $C_2$-$C_6$ alkyl group, an aryl $C_1$-$C_6$ alkyl group, a heteroaryl $C_1$-$C_6$ alkyl group, an aryl group or a heteroaryl group,
R2 is an acyl group R'C(O), in which R' stands for a $C_1$-$C_6$ alkyl group, a $C_2$-$C_6$ hydroxyalkyl group, a $C_1$-$C_6$ alkoxy $C_2$-$C_6$ alkyl group, a carboxy $C_1$-$C_6$ alkyl group, an aryl $C_1$-$C_6$ alkyl group or a heteroaryl $C_1$-$C_6$ alkyl group,
R3, R4 and R5 are, independently of one another, a hydrogen atom, a hydroxyl group, an amino group, a di-($C_1$-$C_6$ alkyl) amino group, a $C_1$-$C_6$ alkyl group, a $C_1$-$C_6$ alkoxy group, a $C_1$-$C_6$ alkoxy $C_2$-$C_6$ alkyl group, a halogen, a nitro group, a carboxy group, a nitrile group, an optionally substituted aryl group, a $C_2$-$C_6$ alkenyl group, an optionally substituted heteroaryl group, and
$X^-$ is a physiologically acceptable anion.

Keratinic fibers (also, keratin fibers) refer to furs, wool, feathers and particularly human hair. Although agents according to the invention are primarily suitable for dyeing keratin fibers, nothing prevents their general use in other fields.

Agents according to the invention contain active substances in a cosmetic carrier. According to the invention, this cosmetic carrier is aqueous, alcoholic or aqueous-alcoholic. For the purposes of dyeing the hair, such carriers are, for example, creams, emulsions, gels and also surfactant-containing foaming solutions, such as, for example, shampoos, foam aerosols or other preparations that are suitable for use on the hair. For the purposes of the present invention, aqueous-alcoholic carriers refer to water-containing solutions comprising 3 to 70% by weight of a $C_1$-$C_4$ alcohol, particularly ethanol or isopropanol, based on total weight of the application mixture. The agents can also contain further organic solvents such as 4-methoxybutanol, ethyl diglycol, 1,2-propylene glycol, n-propanol, n-butanol, n-butylene glycol, glycerin, diethylene glycol monoethyl ether, and diethylene glycol mono-n-butyl ether. Preference here is given to all water-soluble organic solvents. In the context of the invention, an aqueous carrier comprises at least 30 wt. %, especially at least 50 wt. % water, based on total weight of the application mixture.

The agent according to the invention contains a cationic acylpyridinium derivative as an ingredient. It concerns a physiologically acceptable salt according to Formula (I),

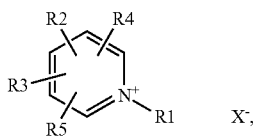

(I)

wherein
R1 is a $C_2$-$C_6$ alkenyl group, a $C_2$-$C_6$ hydroxyalkyl group, a $C_1$-$C_6$ alkoxy $C_2$-$C_6$ alkyl group, a carboxy $C_1$-$C_6$ alkyl group, an aryl $C_1$-$C_6$ alkyl group, a heteroaryl $C_1$-$C_6$ alkyl group, an aryl group or a heteroaryl group,
R2 is an acyl group R'C(O), wherein R' is a $C_1$-$C_6$ alkyl group, a $C_2$-$C_6$ hydroxyalkyl group, a $C_1$-$C_6$ alkoxy $C_2$-$C_6$ alkyl group, a carboxy $C_1$-$C_6$ alkyl group, an aryl $C_1$-$C_6$ alkyl group or a heteroaryl $C_1$-$C_6$ alkyl group,
R3, R4 and R5 are, independently of one another, a hydrogen atom, a hydroxyl group, an amino group, a di-($C_1$-$C_6$ alkyl) amino group, a $C_1$-$C_6$ alkyl group, a $C_1$-$C_6$ alkoxy group, a $C_1$-$C_6$ alkoxy $C_2$-$C_6$ alkyl group, a halogen, a nitro group, a carboxy group, a nitrile group, an optionally substituted aryl group, a $C_2$-$C_6$ alkenyl group, an optionally substituted heteroaryl group, and
$X^-$ is a physiologically acceptable anion.

Examples of the R1, R2, R3, R4, R5 and R' groups in Formula (I) include:
for a $C_1$-$C_6$ alkyl group: methyl, ethyl, propyl, i-propyl, n-butyl, s-butyl, t-butyl, i-butyl, n-pentyl, neo-pentyl, particularly methyl, ethyl and i-propyl;
for a $C_2$-$C_6$ alkenyl group: ethenyl, allyl, (Z)-propen-1-yl, (E)-propen-1-yl, propen-2-yl, (E)-buten-1-yl, (Z)-buten-1-yl, (E)-but-2-en-1-yl, (Z)-but-2-en-1-yl, but-3-en-1-yl, but-2-en-2-yl, but-2-en-3-yl, pent-4-en-1-yl, hex-4-en-1-yl, particularly allyl and but-3-en-1-yl;
for a $C_2$-$C_6$ hydroxyalkyl group: $CH_2CH_2OH$, $CH_2CH_2CH_2OH$, $CH_2CH(OH)CH_3$, $CH_2CH_2CH_2CH_2OH$, particularly $CH_2CH_2OH$ and $CH_2CH_2CH_2OH$;
for a $C_1$-$C_6$ alkoxy group: $OCH_3$, $OCH_2CH_3$, $OCH_2CH_2CH_3$, $OCH(CH_3)_2$, $OCH_2CH_2CH_2CH_3$, $OCH_2CH(CH_3)_2$, $OCH(CH_3)CH_2CH_3$, $OC(CH_3)_3$, particularly a methoxy or ethoxy group;
for a $C_1$-$C_6$ alkoxy $C_2$-$C_6$ alkyl group: $CH_2CH_2OCH_3$, $CH_2CH_2CH_2OCH_3$, $CH_2CH_2OCH_2CH_3$, $CH_2CH_2CH_2OCH_2CH_3$, $CH_2CH_2OCH(CH_3)_2$, $CH_2CH_2CH_2OCH(CH_3)_2$;
for a carboxy $C_1$-$C_6$ alkyl group: $CH_2CO_2H$, $CH_2CH_2CO_2H$, $CH_2CH_2CH_2CO_2H$, $CH_2CH(CH_3)CO_2H$ or one of the physiologically acceptable salts thereof;
for an aryl $C_1$-$C_6$ alkyl group: benzyl, 1-phenylethyl, 2-phenylethyl;
for a di-($C_1$-$C_6$ alkyl)amino group: $N(CH_3)_2$, $N(CH_3)CH_2CH_3$, $N(CH_2CH_3)_2$;
for a heteroaryl $C_1$-$C_6$ alkyl group: (pyridin-2-yl)methyl, (pyridin-3-yl)methyl, (pyridin-4-yl)methyl, (pyridin-2-yl)ethyl, (pyrimidin-4-yl)methyl, (imidazol-1-yl)methyl, (imidazol-2-yl)methyl, (imidazol-4-yl)methyl, (thiazol-4-yl)methyl;
for a heteroaryl group: pyridin-2-yl, pyridin-3-yl, pyridin-4-yl, pyrimidin-4-yl, imidazol-1-yl, imidazol-2-yl, imidazol-4-yl, thiazol-4-yl, thiazol-5-yl, pyrrol-1-yl, pyrrol-2-yl, pyrrol-3-yl, pyrazol-1-yl, pyrazol-3-yl, pyrazol-4-yl, 1,2,3-triazol-1-yl, 1,2,3-triazol-4-yl;
for an aryl group: phenyl, naphthalen-1-yl and naphthalen-2-yl; and
for halogen: fluorine, chlorine, bromine, iodine, particularly chlorine.

A preferred embodiment of the present invention is one wherein R1 in Formula (I) is a $C_1$-$C_6$ alkyl group, a $C_2$-$C_6$ alkenyl group, or a $C_2$-$C_6$ hydroxyalkyl group.

Preferred compounds are those wherein R2 in Formula (I) is an acyl group R'C(O) wherein R' is a $C_1$-$C_6$ alkyl group, particularly methyl. Quite particularly preferred compounds according to Formula (I) include an R2 group that is an acyl group R'C(O) in the 4- or 2-position. These particularly preferred embodiments of the compound according to Formula (I) are illustrated by Formulae (1a) and (1b):

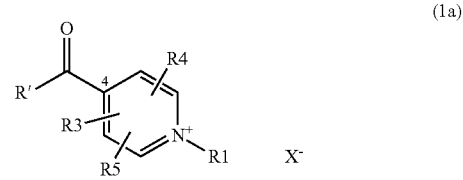

(1a)

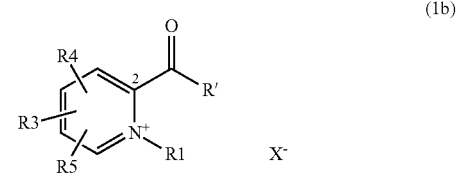

(1b)

R1, R3, R4, R5 and R' are defined as described above. Furthermore, it can be advantageous when R3, R4 and R5 in Formula (I) are each hydrogen.

Preferably, $X^-$ in Formula (I) is chosen from halide (chloride, bromide, iodide), benzene sulfonate, p-toluene sulfonate, ($C_2$ to $C_4$) alkane sulfonate, trifluoromethane sulfonate, acetate, trifluoroacetate, perchlorate, ½ sulfate, hydrogen sulfate, tetrafluoroborate, hexafluorophosphate, hexafluorozincate or tetrafluorozincate.

Even more preferably, the physiologically acceptable anion X⁻ is a halide ion (particularly chloride or bromide), hydrogen sulfate, ½ sulfate, p-toluene sulfonate, benzene sulfonate or acetate.

Particularly preferred cationic acylpyridinium derivatives of general Formula (I) are

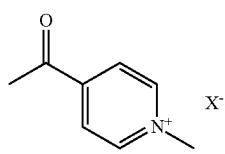

salts of 4-acetyl-1-methylpyridinium;

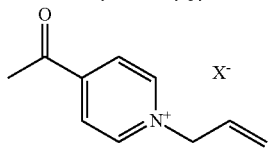

salts of 4-acetyl-1-allylpyridinium;

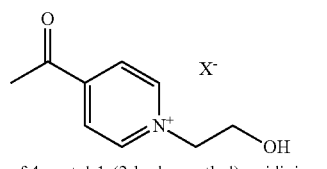

salts of 4-acetyl-1-(2-hydroxyethyl)pyridinium;

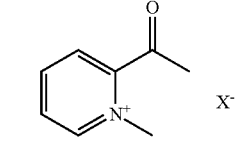

salts of 2-acetyl-1-methylpyridinium;

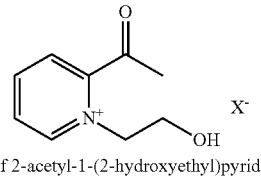

salts of 2-acetyl-1-(2-hydroxyethyl)pyridinium;

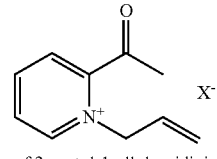

salts of 2-acetyl-1-allylpyridinium;

wherein each X⁻ assumes the meanings according to structure (I), or the meaning of the previous cited embodiments.

In particular, those agents are quite particularly preferred which have at least one acylpyridinium derivative according to Formula (I) chosen from 4-acetyl-1-methylpyridinium p-toluene sulfonate, 4-acetyl-1-methylpyridinium benzene sulfonate, 4-acetyl-1-methylpyridinium bromide, 4-acetyl-1-methylpyridinium chloride, 4-acetyl-1-methylpyridinium hydrogen sulfate, 4-acetyl-1-methylpyridinium acetate, 4-acetyl-1-allylpyridinium p-toluene sulfonate, 4-acetyl-1-allylpyridinium benzene sulfonate, 4-acetyl-1-allylpyridinium bromide, 4-acetyl-1-allylpyridinium chloride, 4-acetyl-1-allylpyridinium hydrogen sulfate, 4-acetyl-1-allylpyridinium acetate, 2-acetyl-1-methylpyridinium p-toluene sulfonate, 2-acetyl-1-methylpyridinium benzene sulfonate, 2-acetyl-1-methylpyridinium bromide, 2-acetyl-1-methylpyridinium chloride, 2-acetyl-1-methylpyridinium hydrogen sulfate, 2-acetyl-1-methylpyridinium acetate, 2-acetyl-1-allylpyridinium p-toluene sulfonate, 2-acetyl-1-allylpyridinium benzene sulfonate, 2-acetyl-1-allylpyridinium bromide, 2-acetyl-1-allylpyridinium chloride, 2-acetyl-1-allylpyridinium hydrogen sulfate, or 2-acetyl-1-allylpyridinium acetate.

The agents quite particularly preferably comprise 2-acetyl-1-methylpyridinium p-toluene sulfonate and/or 4-acetyl-1-methylpyridinium p-toluene sulfonate as the acylpyridinium derivative.

The agents contain acylpyridinium derivatives according to Formula (I) in amounts of 0.01 to 15 wt. %, preferably 0.1 to 12 wt. % and quite particularly preferably 0.5 to 5 wt. %, based on total weight of the ready-to-use agent.

Agents according to the invention contain an oxidation dye precursor as a further ingredient. Based on their mechanistic behavior during actual dye formation, oxidation dye precursors are divided into developer type precursors and coupler type precursors. In a preferred embodiment, the agents contain at least one developer type oxidation dye precursor and/or coupler type oxidation dye precursor. Dyes according to the invention preferably contain at least one developer type oxidation dye precursor and at least one coupler type oxidation dye precursor. The developer and coupler components are usually employed in free form. For substances with amino groups, it can however be preferred to use them in salt form, especially in the form of hydrochlorides and hydrobromides or sulfates.

Preferred p-phenylenediamines are chosen from one or more of p-phenylenediamine, p-toluoylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)-aniline, N,N-bis-(2-hydroxyethyl)-p-phenylenediamine, 4-N,N-bis-(2-hydroxyethyl)-amino-2-methylaniline, 4-N,N-bis-(2-hydroxyethyl)-amino-2-chloroaniline, 2-(2-hydroxyethyl)-p-phenylenediamine, dihydroxyethyl)-p-phenylenediamine, 2-fluoro-p-phenylenediamine, 2-isopropyl-p-phenylenediamine, N-(2-hydroxypropyl)-p-phenylenediamine, 2-hydroxymethyl-p-phenylenediamine, N,N-dimethyl-3-methyl-p-phenylenediamine, N-ethyl-N-2-hydroxyethyl-p-phenylenediamine, N-(2,3-dihydroxypropyl)-p-phenylenediamine, N-(4'-aminophenyl)-p-phenylenediamine, N-phenyl-p-phenylenediamine, 2-(2-hydroxyethyloxy)-p-phenylenediamine, 2-methoxymethyl-p-phenylenediamine, 2-(2-acetylaminoethyloxy)-p-phenylenediamine, N-(2-methoxyethyl)-p-phenylenediamine, N-(4-amino-3-methylphenyl)-N-[3-(1H-imidazol-1-yl)propyl]amine, 5,8-diaminobenzo-1,4-dioxane as well as their physiologically acceptable salts. Particularly preferred p-phenylenediamine derivatives are chosen from at least one of p-phenylenediamine, p-toluoylenediamine, 2-(2-hydroxyethyl)-p-phenylenediamine, dihydroxyethyl)-p-phenylenediamine, N,N-bis-(2-hydroxyethyl)-p-phenylenediamine, N-(4-amino-3-methylphenyl)-N-[3-(1H-imidazol-1-yl)propyl]amine, and 2-methoxymethyl-p-phenylenediamine, as well as the physiologically acceptable salts of these compounds.

According to the invention, it may also be preferred to use compounds as the developer component which have at least two aromatic nuclei substituted by amino and/or hydroxyl groups. Preferred binuclear developer components are especially chosen from at least one of the following compounds: N,N'-bis-(2-hydroxyethyl)-N,N'-bis-(4'-aminophenyl)-1,3-diaminopropan-2-ol, N,N'-bis-(2-hydroxyethyl)-N,N'-bis-(4'-aminophenyl)ethylenediamine, N,N-bis-(4'-aminophenyl)tetramethylenediamine, N,N'-bis-(2-hydroxyethyl)-N,N'-bis-(4'-aminophenyl)-tetramethylenediamine, N,N'-bis-(4-(methylamino)phenyl)tetramethylenediamine, N,N'-diethyl-N,N'-bis-(4'-amino-3'-methylphenyl)-ethylenediamine, bis-(2-hydroxy-5-aminophenyl)methane, N,N-bis-(4'-aminophenyl)-1,4-diazacycloheptane, N,N'-bis-(2-hydroxy-5-aminobenzyl)piperazine, N-(4'-aminophenyl)-p-phenylenediamine and 1,10-bis-(2',5'-diaminophenyl)-1,4,7,10-tetraoxadecane and their physiologically acceptable salts. Particularly preferred binuclear developer components are selected from among N,N'-bis-(2-hydroxyethyl)-N,N-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis(4-aminophenyl)-1,4-diazacycloheptane, 1,10-bis-(2,5-diaminophenyl)-1,4,7,10-tetraoxadecan or one of the physiologically acceptable salts of these compounds.

Moreover, according to the invention, it may be preferred to use a p-aminophenol derivative or one of its physiologically acceptable salts as the developer component. Preferred p-aminophenols include p-aminophenol, N-methyl-p-aminophenol, 4-amino-3-methyl-phenol, 4-amino-3-fluorophenol, 2-hydroxymethylamino-4-aminophenol, 4-amino-3-hydroxymethylphenol, 4-amino-2-(2-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(2-hydroxyethylaminomethyl)phenol, 4-amino-2-(1,2-dihydroxyethyl)phenol, 4-amino-2-fluorophenol, 4-amino-2-chlorophenol, 4-amino-2,6-dichlorophenol, 4-amino-2-(diethylaminomethyl)phenol as well as their physiologically acceptable salts. p-Aminophenol, 4-amino-3-methylphenol, 4-amino-2-aminomethylphenol, 4-amino-2-(1,2-dihydroxyethyl)phenol and 4-amino-2-(diethylaminomethyl)phenol are particularly preferred.

Furthermore, the developer component can be chosen from o-amino phenol and its derivatives, such as 2-amino-4-methylphenol, 2-amino-5-methylphenol or 2-amino-4-chlorophenol.

In addition, the developer component can be chosen from heterocyclic developer components, such as pyridine, pyrimidine, pyrazole, pyrazole-pyrimidine derivatives and their physiologically acceptable salts. Preferred pyrimidine derivatives are chosen from the compounds 2,4,5,6-tetraminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine and 2,5,6-triaminopyrimidine. Preferred pyrazole derivatives are inventively selected from 4,5-diamino-1-methylpyrazole, 4,5-diamino-1-(2-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-t-butyl-1-methylpyrazole, 4,5-diamino-1-t-butyl-3-methylpyrazole, 4,5-diamino-1-(2-hydroxyethyl)-3-methylpyrazole, 4,5-diamino-1-ethyl-3-methylpyrazole, 4,5-diamino-1-ethyl-3-(4-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2-aminoethyl)amino-1,3-dimethylpyrazole, as well as their physiologically acceptable salts, especially however 4,5-diamino-1-(2-hydroxyethyl)pyrazole. Preferred pyrazolopyrimidine derivatives are especially selected from pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidine-7-ol; 3-aminopyrazolo[1,5-a]pyrimidine-5-ol; 2-(3-aminopyrazolo[1,5-a]pyrimidine-7-ylamino)ethanol; 2-(7-aminopyrazolo[1,5-a]pyrimidine-3-ylamino)ethanol; 2-[(3-aminopyrazolo[1,5-a]pyrimidine-7-yl)-(2-hydroxyethyl)amino]ethanol; 2-[(7-aminopyrazolo[1,5-a]pyrimidine-3-yl)-(2-hydroxyethyl)-amino]ethanol; 5,6-dimethylpyrazolo[1,5-a]pyrimidine-3,7-diamine; 2,6-dimethylpyrazolo[1,5-a]-pyrimidine-3,7-diamine; 3-amino-7-dimethylamino-2,5-dimethylpyrazolo[1,5-a]pyrimidine, as well as their physiologically acceptable salts and their tautomeric forms.

Particularly preferred developer components are chosen from at least one compound from p-phenylenediamine, p-toluoylenediamine, 2-(2-hydroxyethyl)-p-phenylenediamine, dihydroxyethyl)-p-phenylenediamine, N,N-bis-(2-hydroxyethyl)-p-phenylenediamine, 2-methoxymethyl-p-phenylenediamine, n-(4-amino-3-methylphenyl)-N-[3-(1h-imidazol-1-yl)propyl]amine, N,N'-bis-(2-hydroxyethyl)-N,N'-bis-(4-aminophenyl)-1,3-diamino-propan-2-ol, bis-(2-hydroxy-5-aminophenyl)methane, 1,3-bis-(2,5-diaminophenoxy)-propan-2-ol, N,N'-bis-(4-aminophenyl)-1,4-diazacycloheptane, 1,10-bis-(2,5-diaminophenyl)-1,4,7,10-tetraoxadecan, p-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)pyrazole, 2,4,5,6-tetraminopyrimidine, 4-hydroxy-2,5,6-triaminopyrimidine, 2-hydroxy-4,5,6-triaminopyrimidine, as well as the physiologically acceptable salts of these compounds. In this regard, quite particularly preferred developer components are p-toluoylenediamine, 2-(2-hydroxyethyl)-p-phenylenediamine, 2-methoxy-methyl-p-phenylenediamine, N-(4-amino-3-methylphenyl)-N-[3-(1H-imidazol-1-yl)propyl]amine, and/or 4,5-diamino-1-(2-hydroxyethyl)pyrazole, as well as the physiologically acceptable salts of these compounds. Developer components are preferably used in an amount of 0.005 to 20% by weight, preferably 0.1 to 5% by weight, based on total ready-to-use oxidation dye agent.

Coupler components by themselves, in the context of oxidative dyeing, typically do not form any significant coloration; rather, they need the presence of developer components. Therefore, when using at least one coupler component, preferably at least one developer component is also used.

Preferred m-aminophenol coupler components are chosen from at least one of 3-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)-amino-2-methylphenol, 3-diethylaminophenol, N-cyclopentyl-3-aminophenol, 1,3-dihydroxy-5-(methylamino)benzene, 3-ethylamino-4-methylphenol, 2,4-dichloro-3-aminophenol, and their physiologically acceptable salts.

Preferred m-diaminophenol coupler components are chosen from at least one of m-phenylenediamine, 2-(2,4-diaminophenoxy)ethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino) ethanol, 2-({3-[(2-hydroxyethyl)-amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(T-hydroxyethyl) aminobenzene, and their physiologically acceptable salts.

Preferred o-diaminobenzene coupler components are chosen from at least one of 3,4-diaminobenzoic acid, 2,3-diamino-1-methylbenzene, and their physiologically acceptable salts.

Preferred di- or trihydroxybenzenes and their derivatives are chosen from at least one of resorcinol, resorcinol monomethyl ether, 2-methylresorcinol, 5-methylresorcinol, 2,5-dimethylresorcinol, 2-chlororesorcinol, 4-chlororesorcinol, pyrogallol and 1,2,4-trihydroxybenzene.

Useful pyridine derivatives are preferably chosen from at least one compound of 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 3,4-diaminopyridine, 2-(2-methoxyethyl)amino-3-amino-6-methoxypyridine, 2-(4'-methoxyphenyl)amino-3-aminopyridine, and their physiologically acceptable salts.

Preferred naphthalene derivatives with at least one hydroxyl group are chosen from at least one of 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihydroxynaphthalene.

Useful indole derivatives are preferably chosen from at least one of 4-hydroxyindole, 6-hydroxyindole, 7-hydroxyindole, and their physiologically acceptable salts. Particularly preferred indoline derivatives are chosen from at least one compound of 4-hydroxyindoline, 6-hydroxyindoline, 7-hydroxyindoline, and their physiologically acceptable salts.

Preferred pyrimidine derivatives are chosen from at least one compound of 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine, 4,6-dihydroxy-2-methylpyrimidine, and their physiologically acceptable salts.

According to the invention, particularly preferred coupler components are chosen from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)-ethanol, 1,3-bis(2,4-diaminophenoxy)propane, 1-methoxy-2-amino-4-(2-hydroxyethylamino)-benzene, 1,3-bis(2,4-diaminophenyl)propane, 2,6-bis(2'-hydroxyethylamino)-1-methylbenzene, 2-({[3-[(2-hydroxyethyl)amino]-4-methoxy-5-methylphenyl}amino)ethanol, 2-({3-[(2-hydroxyethyl)amino]-2-methoxy-5-methylphenyl}amino) ethanol, 2-([{3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl) aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or their physiologically acceptable salts. In this regard, resorcinol, 2-methylresorcinol, 5-amino-2-methylphenol, 3-aminophenol, 2-(2,4-diaminophenoxy)ethanol, 1,3-bis(2,4-diaminophenoxy)propane, 1-methoxy-2-amino-4-(2'-hydroxyethylamino)benzene, 2-amino-3-hydroxypyridine and 1-naphthol as well as their physiologically acceptable salts are quite particularly preferred. Coupler components are preferably used in an amount of 0.005 to 20% by weight, preferably 0.1 to 5% by weight, based on total ready-to-use oxidation dye agent.

According to the present invention, the following combinations of developer type oxidation dye precursors and coupler type oxidation dye precursors are particularly preferred. However, further dye precursors can also be combined with the oxidation dye precursors cited as a combination: p-toluoylenediamine/resorcinol; p-toluoylenediamine/2-methylresorcinol; p-toluoylenediamine/5-amino-2-methylphenol; p-toluoylenediamine/3-aminophenol; p-toluoylenediamine/2-(2,4-diaminophenoxy)ethanol; p-toluoylenediamine/1,3-bis(2,4-diaminophenoxy)propane; p-toluoylenediamine/1-methoxy-2-amino-4-(2-hydroxyethylamino)-benzene; p-toluoylenediamine/2-amino-3-hydroxypyridine; p-toluoylenediamine/1-naphthol; 2-(2-hydroxyethyl)-p-phenylenediamine/resorcinol; 2-(2-hydroxyethyl)-p-phenylenediamine/2-methylresorcinol; 2-(2-hydroxyethyl)-p-phenylenediamine/5-amino-2-methylphenol; 2-(2-hydroxyethyl)-p-phenylenediamine/3-aminophenol; 2-(2-hydroxyethyl)-p-phenylenediamine/2-(2,4-diaminophenoxy)ethanol; 2-(2-hydroxyethyl)-p-phenylenediamine/1,3-bis(2,4-diaminophenoxy)propane; 2-(2-hydroxyethyl)-p-phenylenediamine/1-methoxy-2-amino-4-(2-hydroxyethylamino)benzene; 2-(2-hydroxyethyl)-p-phenylenediamine/2-amino-3-hydroxypyridine; 2-(2-hydroxyethyl)-p-phenylenediamine/1-naphthol; 2-methoxymethyl-p-phenylenediamine/resorcinol; 2-methoxymethyl-p-phenylenediamine/2-methylresorcinol; 2-methoxymethyl-p-phenylenediamine/5-amino-2-methylphenol; 2-methoxymethyl-p-phenylenediamine/3-aminophenol; 2-methoxymethyl-p-phenylenediamine/2-(2,4-diaminophenoxy)ethanol; 2-methoxymethyl-p-phenylenediamine/1,3-bis(2,4-diaminophenoxy)propane; 2-methoxymethyl-p-phenylenediamine/1-methoxy-2-amino-4-(2-hydroxyethylamino)benzene; 2-methoxymethyl-p-phenylenediamine/2-amino-3-hydroxypyridine; 2-methoxymethyl-p-phenylenediamine/1-naphthol; N-(4-amino-3-methylphenyl)-N-[3-(1H-imidazol-1-yl)propyl]amine/resorcinol; N-(4-amino-3-methylphenyl)-N-[3-(1H-imidazol-1-yl)propyl]amine/2-methylresorcinol; N-(4-amino-3-methylphenyl)-N-[3-(1H-imidazol-1-yl)propyl]-amine/5-amino-2-methylphenol; N-(4-amino-3-methylphenyl)-N-[3-(1H-imidazol-1-yl)propyl]-amine/3-aminophenol; N-(4-amino-3-methylphenyl)-N-[3-(1H-imidazol-1-yl)propyl]amine/2-(2,4-diaminophenoxy) ethanol; N-(4-amino-3-methylphenyl)-N-[3-(1H-imidazol-1-yl)propyl]-amine/1,3-bis(2,4-diaminophenoxy)propane; N-(4-amino-3-methylphenyl)-N-[3-(1H-imidazol-1-yl)propyl]amine 1-methoxy-2-amino-4-(2-hydroxyethylamino) benzene; N-(4-amino-3-methylphenyl)-N-[3-(1H-imidazol-1-yl)propyl]amine/2-amino-3-hydroxypyridine; N-(4-amino-3-methyl-phenyl)-N-[3-(1H-imidazol-1-yl)propyl]amine/1-naphthol; 4,5-diamino-1-(2-hydroxyethyl)-pyrazole/resorcinol; 4,5-diamino-1-(2-hydroxyethyl)

pyrazole/2-methylresorcinol; 4,5-diamino-1-(2-hydroxyethyl)pyrazole/5-amino-2-methylphenol; 4,5-diamino-1-(2-hydroxyethyl)pyrazole/3-aminophenol; 4,5-diamino-1-(2-hydroxyethyl)pyrazole/2-(2,4-diaminophenoxy)ethanol; 4,5-diamino-1-(2-hydroxyethyl)pyrazole/1,3-bis(2,4-diaminophenoxy)propane; 4,5-diamino-1-(2-hydroxyethyl)pyrazole/1-methoxy-2-amino-4-(2-hydroxyethylamino)benzene; 4,5-diamino-1-(2-hydroxyethyl)pyrazole/2-amino-3-hydroxypyridine; and 4,5-diamino-1-(2-hydroxyethyl)pyrazole/1-naphthol.

According to the present invention, it is quite particularly advantageous when the agents contain at least one of the aforementioned oxidation dye precursor combinations together with 4-acetyl-1-methylpyridinium p-toluene sulfonate as the acylpyridinium derivative. According to the present invention, it is likewise quite particularly advantageous when the agents contain at least one of the aforementioned oxidation dye precursor combinations together with 2-acetyl-1-methylpyridinium p-toluene sulfonate as the acylpyridinium derivative.

According to the present invention, oxidation dye precursors are used in an amount of 0.005 to 20 wt. %, preferably 0.05 to 5 wt. %, and particularly preferably from 0.1 to 5 wt. %, based on total ready-to-use oxidation dye agent. According to the present invention, it is particularly preferred when the combination of all oxidation dye precursors and acylpyridinium derivatives according to Formula (I) are used in an amount of 0.05 to 20 wt. %, preferably 0.1 to 15 wt. % and particularly preferably from 0.5 to 12 wt. %, based on total ready-to-use oxidation dye agent. Here, developer and coupler components are generally used in approximately molar amounts relative to one another. Although molar use has proven to be expedient, a certain excess of individual oxidation dye precursors is not disadvantageous, meaning that developer components and coupler components can be present in a molar ratio of from 1 to 0.5 to 1 to 3, particularly 1 to 1 to 1 to 2.

In another embodiment, the agent contains at least one more additional chromophoric component beside the oxidation dye precursors. The additional chromophoric component is preferably chosen from at least one substantive dye. These are dyes that are directly absorbed onto the hair and do not require any oxidative process to develop the color. Substantive dyes are typically nitrophenylenediamines, nitroaminophenols, azo dyes, anthraquinones or indophenols.

The substantive dyes are preferably used in quantities of 0.001 to 20 wt. %, based on total end-use preparation. The total amount of substantive dyes is preferably no more than 20 wt. %. Substantive dyes can be classified as anionic, cationic and non-ionic substantive dyes.

Preferred anionic substantive dyestuffs are known compounds with the international designations or trade names tetrabromophenol blue, Acid Yellow 1, Acid Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1 and Acid Black 52.

Preferred cationic substantive dyes include cationic triphenylmethane dyes such as Basic Blue 7, Basic Blue 26, Basic Violet 2 and Basic Violet 14, aromatic systems that are substituted with a quaternary nitrogen group, such as Basic Yellow 57, Basic Red 76, Basic Blue 99, Basic Brown 16 and Basic Brown 17, as well as substantive dyes containing a heterocycle having at least one quaternary nitrogen atom. Compounds also known under the names Basic Yellow 87, Basic Orange 31 and Basic Red 51 are quite particularly preferred cationic substantive dyes.

Non-ionic nitro and quinone dyes and neutral azo dyes are particularly suitable as non-ionic substantive dyes. Preferred non-ionic substantive dyes include compounds known under the international designations or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)-amino-2-nitrobenzene, 3-nitro-4-[(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]-benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid, and 2-chloro-6-ethylamino-4-nitrophenol.

It is not required that each oxidation dyestuff precursors or substantive dyestuffs be pure compounds. In fact, the hair colorants, due to the manufacturing processes for individual dyes, may contain minor quantities of even more components to the extent that they have no detrimental influence on the coloration result or that they must be excluded on other grounds (e.g., toxicological).

Generally, packaging of the dye agent is not limited in any way. Agents according to the invention are usually packaged as a 1-component agent (A) which, immediately prior to application, is optionally blended with a second preparation containing, for example, an oxidizing agent. However, in certain cases it is also preferable when the product is packaged as a 2-component agent. Accordingly, in a preferred embodiment, the agents are packaged so that the acylpyridinium derivative according to Formula (I) is packaged as one of the components in a preparation (A2) separate from preparation (A1) containing the oxidation dye precursor. Both of these preparations are blended prior to use and an optional oxidizing agent preparation (B) can be additionally added. Here it can be advantageous to first mix the oxidizing agent preparation (B) and preparation (A2) containing the acylpyridinium derivative, and then add the preparation containing oxidation dye precursor (A1). Likewise, it is possible to first mix the preparation (A2) containing the acylpyridinium derivative with preparation (A1) containing the oxidation dye precursor, and then add the oxidizing agent preparation (B).

For oxidative dyeing, color development can occur with atmospheric oxygen. However, it is preferred to use a chemical oxidizing agent, particularly when a lightening effect on human hair is desired in addition to the dyeing. This lightening effect may be desired independently of the dyeing method. Persulfates, peroxydisulfates, chlorites, hypochlorites and particularly hydrogen peroxide or and/or one of its solid addition products on organic or inorganic compounds can be used as the oxidizing agent. In order to prevent a premature, unwanted reaction of the oxidation dye precursor with the oxidizing agent, the oxidation dye precursor and the oxidizing agent itself are advantageously packaged separately from one another and first brought into contact directly prior to use.

Another subject matter of the present invention is therefore an agent produced directly prior to use by blending at least two preparations, wherein the at least two preparations are provided in at least two separately packaged containers, and wherein one container contains a dye (A) that has in a cosmetic carrier at least one oxidation dye precursor as well as at least one acylpyridinium derivative according to Formula (I), and an additional container that has an oxidizing agent preparation (B) comprising at least one oxidizing agent.

A particular subject matter of the present invention is moreover an agent produced directly prior to use by blending at least three preparations, wherein the at least three preparations are provided in at least three separately packaged containers, and wherein one container contains a dye (A1) that has in a cosmetic carrier at least one oxidation dye precursor, a second container contains an agent (A2) that has in a cosmetic carrier at least one acylpyridinium derivative according to Formula (I), and an additional container that has an oxidizing agent preparation (B) comprising at least one oxidizing agent.

Oxidizing agent preparation (B) preferably includes hydrogen peroxide and/or one of its solid addition products on organic or inorganic compounds, such as urea, melamine and sodium borate, as the oxidizing agent. The amount of oxidizing agent in the ready-to-use agent is preferably 0.5 to 12 wt. %, preferably 2 to 10 wt. %, particularly preferably 3 to 6 wt. % (calculated as 100% conc. $H_2O_2$), based on total ready-to-use agent.

Such oxidizing agent preparations are preferably aqueous, free-flowing oxidizing agent preparations. In this regard, preferred preparations are those wherein the free-flowing oxidizing agent preparation contains 40 to 90 wt. %, preferably 50 to 85 wt. %, more preferably 55 to 80 wt. %, even more preferably 60 to 77.5 wt. % and particularly 65 to 75 wt. % water, based on total weight of the preparation.

According to the invention, the oxidation dyeing agent can also be applied to the hair together with a catalyst that activates oxidation of the dye precursors (e.g., by atmospheric oxygen). Such catalysts include certain enzymes, iodides, quinones or metal ions. Suitable enzymes are, for example, peroxidases, which can considerably enhance the effect of small amounts of hydrogen peroxide. An addition of certain metal ions or metal complexes can likewise be preferred in order to obtain intensive, long-lasting colorations. Suitable metal ions include $Zn^{2+}$, $Cu^{2+}$, $Fe^{2+}$, $Fe^{3+}$, $Mn^{2+}$, $Mn^{4+}$, $Li^+$, $Mg^{2+}$, $Ca^{2+}$, $Ce^{4+}$, $V^{3+}$, $Co^{2+}$, $Ru^{3+}$ and $Al^{3+}$.

In addition, it has proven advantageous when the oxidizing agent preparations contain (b) at least one stabilizer or complexant. Particularly preferred stabilizers are phenacetin, alkali benzoates (sodium benzoate) and salicylic acid. The addition of complexants is also inventively preferred. Preferred complexants are nitrogen-containing polycarboxylic acids, especially EDTA, and phosphonates, preferably hydroxyalkane or aminoalkane phosphonates and especially 1,1-hydroxyethane-1,1-diphosphonate (HEDP) and/or ethylenediaminetetramethylene phosphonate (EDTMP) and/or diethylenetriaminepentamethylene phosphonate (DTPMP) or their sodium salts.

The oxidizing agent preparation can contain additional auxiliaries and additives in addition to the actual oxidizing agent. Thus, it is preferred when the oxidizing agent preparation contains at least one thickener. In general, there are no limitations regarding this thickener. Both organic and inorganic thickeners can be used.

In order to further increase the lightening power, at least one optionally hydrated $SiO_2$ compound can be added to the agent. Although small amounts of the optionally hydrated $SiO_2$ compounds already increase lightening power, it may be preferred to use the optionally hydrated $SiO_2$ compounds in amounts of 0.05 to 15 wt. %, more preferably in amounts of 0.15 to 10 wt. %, and quite preferably in amounts of 0.2 to 5 wt. %, based on the anhydrous agent according to the invention. Regarding the optionally hydrated $SiO_2$ compounds, the present invention is not in general subject to any limitations. Preference is given to silicic acids, their oligomers and polymers, and their salts. According to the invention, $SiO_2$ compounds are preferably used in the form of silica gels or particularly preferably as a water glass. Particularly preferred water glasses are sold, inter alia, by Henkel under the names Ferrosil® 119, Natronwasserglas 40/42, Portil® A, Portil® AW and Portil® W, and by Akzo Nobel under the name Britesil® C20.

Oxidizing agent preparation (B) and/or preparation (A) or preparations (A1) and (A2) are preferably made up as free-flowing preparations. An emulsifier or surfactant is also preferably added to free-flowing preparation (A), respectively (A1) and (A2), wherein surface active substances are designated surfactant or emulsifier depending on their field of application, and are chosen from anionic, cationic, zwitterionic, amphoteric and non-ionic surfactants and emulsifiers. These substances are described in detail below.

Suitable anionic surfactants include all anionic surface-active materials suitable for use on the human body. Preferred anionic surfactants are alkyl sulfates, alkyl ether sulfates and ether carboxylic acids containing 10 to 18 carbon atoms in the alkyl group and up to 12 glycol ether groups in the molecule.

Suitable zwitterionic emulsifiers are betaines such as N-alkyl-N,N-dimethylammonium glycinates, N-acyl-aminopropyl-N,N-dimethylammonium glycinates and 2-alkyl-3-carboxymethyl-3-hydroxyethyl-imidazolines, each having 8 to 18 carbon atoms in the alkyl or acyl group, as well as cocoacylaminoethylhydroxyethylcarboxymethyl glycinate. A preferred zwitterionic surfactant is the fatty acid amide derivative known under the INCI name Cocamidopropyl Betaine.

Examples of suitable ampholytic surfactants are N-alkylglycines, N-alkylamino propionic acids, N-alkylamino butyric acids, N-alkylimino dipropionic acids, N-hydroxyethyl-N-alkylamidopropylglycine, N-alkyltaurines, N-alkylsarcosines, 2-alkylamino propionic acids and alkylamino acetic acids, each with about 8 to 24 carbon atoms in the alkyl group. Particularly preferred amphoteric surfactants are N-cocoalkylamino propionate, cocoacylaminoethylamino propionate, and C12-18 acyl sarcosine.

Furthermore, it has proven advantageous when the dye and lightening agents contain additional, non-ionic surface active substances. $C_8$-$C_{22}$ alkyl mono- and oligo-glycosides and their ethoxylated analogs are particularly suitable non-ionic surfactants. In particular, the non-ethoxylated compounds have proven to be suitable. Alkylene oxide addition products on saturated, linear fatty alcohols and fatty acids, each with 2 to 30 moles ethylene oxide per mole fatty alcohol or fatty acid, have proven to be additional preferred non-ionic surfactants. Preparations with excellent properties are also obtained when they contain fatty acid esters of ethoxylated glycerin as the non-ionic surfactant.

Anionic, non-ionic, zwitterionic or amphoteric surfactants are used in amounts of 0.1 to 45 wt. %, preferably 1 to 30 wt. % and more preferably 1 to 15 wt. %, based on total amount of ready-to-use agent.

According to the invention, cationic surfactants of the type quaternary ammonium compounds, esterquats and amido amines are likewise preferred. Preferred quaternary ammonium compounds are ammonium halides, especially chlorides and bromides, such as alkyltrimethylammonium chlorides, dialkyldimethyl ammonium chlorides and trialkylmethylammonium chlorides, as well as imidazolium compounds known under the INCI names Quaternium-27 and Quaternium-83. Long alkyl chains of the abovementioned surfactants have preferably 10 to 18 carbon atoms. Quaternized protein hydrolyzates illustrate further usable cationic surfactants. Alkylamido amines are normally manufactured by amidation of natural or synthetic fatty acids and fatty acid fractions with dialkylamino amines. According to the invention, a particularly suitable compound from this substance group is stearamidopropyldimethylamine, commercially available under the designation Tegamid® S 18. Quaternary ester compounds or "ester-quats" are likewise highly biologically degradable. Such products are marketed, for example, under the trade names Stepantex®, Dehyquart® and Armocare®. The agents preferably contain cationic surfactants in amounts of 0.05 to 10 wt. %, based on total agent. Quantities of 0.1 to 5% by weight are particularly preferred.

In a preferred embodiment, non-ionic, zwitterionic and/or amphoteric surfactants as well as mixtures thereof can be preferred.

In a further preferred embodiment of the invention, the action of the active can be increased by emulsifiers. Such emulsifiers include addition products of 4 to 30 mole ethylene oxide and/or 0 to 5 mole propylene oxide to linear fatty alcohols containing 8 to 22 carbon atoms, to fatty acids with 12 to 22 carbon atoms, and to alkyl phenols with 8 to 15 carbon atoms in the alkyl group; $C_{12}$-$C_{22}$ fatty acid mono- and diesters of addition products of 1 to 30 moles ethylene oxide on glycerin; $C_8$-$C_{22}$ alkyl-mono- and oligoglycosides; mixtures of alkyl (oligo) glucosides and fatty alcohols; addition products of 5 to 60 moles ethylene oxide to castor oil and to hydrogenated castor oil; partial esters of polyols containing 3 to 6 carbon atoms with saturated fatty acids containing 8 to 22 carbon atoms; sterols (zoosterols, phytosterols, mycosterols); phospholipids; fatty acid esters of sugars and sugar alcohols, such as sorbitol; polyglycerins and polyglycerine derivatives; as well as linear and branched fatty acids containing 8 to 30 carbon atoms and their Na, K, ammonium, Ca, Mg and Zn salts.

The agents preferably contain emulsifiers in amounts of 0.1 to 25 wt. %, particularly 0.5-15 wt. %, based on total ready-to-use agent.

Agents according to the invention preferably contain at least one non-ionic emulsifier or surfactant with an HLB value of 8 to 18, according to the definitions listed in *Römpp-Lexikon Chemie* (Ed. J. Falbe, M. Regitz), $10^{th}$ Ed., Georg Thieme Verlag Stuttgart, New York, (1997), p. 1764. Non-ionic emulsifiers with an HLB value of 10 to 15 can be particularly preferred.

Exemplary additional active substances, adjuvants and additives which can be used in agents according to the invention are: non-ionic polymers; silicones such as polyalkylsiloxanes (like Dimethicone or Cyclomethicone), polyarylsiloxanes and/or polyalkylarylsiloxanes; cationic polymers; zwitterionic and amphoteric polymers; anionic polymers like polyacrylic acids; thickeners like agar-agar, guar gum, alginates, xanthane gum, gum arabica, karaya gum, locust bean flour, linseed gums, dextrans, cellulose derivatives, e.g., methyl cellulose, hydroxyalkyl cellulose and carboxymethyl cellulose, starch fractions and derivatives like amylose, amylopectin and dextrins, clays such as bentonite or synthetic hydrocolloids such as polyvinyl alcohol; structurants such as glucose, maleic acid and lactic acid; hair conditioning compounds like phospholipids, e.g., soya lecithin, egg lecithin and cephalin, as well as silicone oils; protein hydrolyzates, particularly elastin, collagen, keratin, milk protein, soya protein and wheat protein, their condensation products with fatty acids as well as quaternized protein hydrolyzates; perfume oils, dimethyl isosorbitol and cyclodextrins; fiber structure improvers, particularly mono-, di- and oligosaccharides, such as glucose, galactose, fructose, fruit sugar and lactose; defoamers such as silicones; dyestuffs to color the agent; anti-dandruff active substances; amino acids and oligopeptides, particularly arginine and/or serine; UV stabilizers; active ingredients such as panthenol, pantothenic acid, allantoin, pyrrolidinone carboxylic acids and salts thereof as well as bisabolol; polyphenols, particularly hydroxycinnamic acids, 6,7-dihydroxycumarine, hydroxybenzoic acids, catechol, tannins, leucoanthocyanidines, anthocyanidines, flavanones, flavones and flavonols; ceramides, preferably sphingolipids or pseudoceramides; vitamins, provitamins and vitamin precursors, particularly A, $B_3$, $B_5$, $B_6$, C, E, F and H; plant extracts such as extracts from green tea, oak bark, stinging nettle, hamamelis, hops, camomile, burdock root, field horsetail, hawthorn, linden flowers, almonds, aloe vera, spruce needles, horse chestnut, sandal wood, juniper, coconut, mango, apricot, lime, litchi, wheat, kiwi, melon, orange, grapefruit, sage, rosemary, birch, malva, lady's smock, common yarrow, thyme, lemon balm, rest-harrow, coltsfoot, marshmallow (althaea), meristem, ginseng and ginger; cholesterol; texturisers such as sugar esters, polyol esters or polyol alkyl ethers; fats and waxes like fatty alcohols, beeswax, montan wax and paraffins; swelling and penetration substances such as glycerin, propylene glycol monoethyl ether, carbonates, hydrogen carbonates, guanidines, ureas, and primary, secondary and tertiary phosphates; opacifiers like latex, styrene/PVP copolymers and styrene/acrylamide copolymers; pearlizers; pigments; propellants like propane-butane mixtures, $N_2O$, dimethyl ether, $CO_2$ and air, as well as antioxidants.

One skilled in the art chooses these additional materials based on the desired properties of the agent. Regarding further optional ingredients and their amounts used, reference is made to relevant handbooks known to one skilled in the art, such as the monograph by K. Schrader, *Grundlagen and Rezepturen der Kosmetika*, $2^{nd}$ Ed., Hüthig Buch Verlag, Heidelberg (1989). Additional active substances and auxiliaries are preferably incorporated into the agents in amounts of 0.0001 to 10 wt. %, particularly 0.0005 to 5 wt. %, based on total weight of the application agent.

In order to further improve the lightening effect, it can be advantageous when the agents further contain a toxicologically harmless bleach co-activator and/or its physiologically acceptable salt. The term "toxicologically harmless" refers to those compounds that do not possess acute toxicity, sub-acute toxicity and chronic toxicity, as well as no carcinogenic, genotoxic or teratogenic action. In the context of the present invention, imidazole is particularly not to be understood as a toxicologically harmless bleach co-activator. This toxicologically harmless bleach co-activator is preferably chosen from aliphatic and/or carbocyclic bleach co-activators.

This toxicologically harmless bleach co-activator preferably contains a hydroxyl group, a carboxylic acid, a sulfuric acid monoester, a phosphoric acid monoester and/or a physiologically acceptable salt thereof as a structural feature.

Should the toxicologically harmless bleach co-activator contain a structural unit that permits a plurality of steric configurations, such as substituted double bonds or asymmetric centers, then in the context of the present invention all possible stereoisomers are included. Optionally, however, it can be preferred to use either only one possible stereoisomer or a mixture of two or more stereoisomers.

Preferred agents contain at least one bleach co-activator according to Formula (II) and/or its physiologically accept able salt as the bleach co-activator and/or its physiologically acceptable salt,

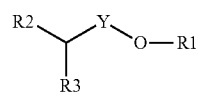

(II)

wherein
Y is a carbonyl group, a direct bond or methylene group,
R1 is hydrogen, a $C_1$-$C_4$ alkyl group, a physiologically acceptable cation or a $SO_3^-$ group or a $PO_3^{2-}$ group,
R2 is an amino, a methylamino, a dimethylamino, a trimethylammonio group, phenyl, benzyl, phenoxymethyl, 1-naphthyl, 2-naphthyl, 2-, 3-, 4-toluoyl, or a R4-O—$(CH_2CH_2O)_n$ group,
wherein R4 is a $C_6$-$C_{20}$ alkyl group and n is a number greater than 15, and
R3 is hydrogen or an optionally branched $C_1$-$C_6$ alkyl group,
with the proviso that, when Y is a carbonyl group,
R1 is hydrogen, a $C_1$-$C_4$ alkyl group or a physiologically acceptable cation,
R2 is an amino, a methylamino, a dimethylamino or a trimethylammonio group, and
R3 is hydrogen or an optionally branched $C_1$-$C_6$ alkyl group,
with the proviso that, when Y is a direct bond,
R1 is hydrogen,
R2 is phenyl, benzyl, phenoxymethyl, 1-naphthyl, 2-naphthyl, 2-, 3- or 4-toluoyl, and
R3 is hydrogen or an optionally branched $C_1$-$C_6$ alkyl group,
with the proviso that, when Y is a methylene group,
R1 is a $SO_3^-$ or a $PO_3^{2-}$ group,
R2 is a R4-O—$(CH_2CH_2O)_n$ group, wherein R4 is a $C_6$-$C_{20}$ alkyl group and n is a number greater than 15, and
R3 is hydrogen.

In particular, preferred agents contain at least one aliphatic amino acid optionally N-methylated or N,N-methylated on its nitrogen atom, and/or its physiologically acceptable salt, as the bleach co-activator. Preferred bleach co-activators are chosen from glycine, N-methylglycine, N,N-dimethylglycine, alanine, N-methylalanine, N,N-dimethylalanine, leucine, N-methylleucine, N,N-dimethylleucine, isoleucine, N-methylisoleucine, N,N-dimethylisoleucine or their physiologically acceptable salts. Glycine and/or its physiologically acceptable salt are quite preferably used as the bleach co-activator in the agent according to the invention.

Preferred agents according to the invention contain at least one aromatic alcohol and/or its physiologically acceptable salt as the bleach co-activator. Benzyl alcohol, 2-phenylethyl alcohol, 1-phenylethyl alcohol, 2-phenoxyethanol, 1-hydroxymethylnaphthalene and/or 2-hydroxymethylnaphthalene may be cited as inventively preferred aromatic alcohols. Benzyl alcohol is a quite particularly preferred aromatic alcohol as the bleach co-activator.

Finally, those agents are preferred that have as the bleach co-activator a physiologically acceptable salt of an alkyl ether sulfate according to Formula (III)

(III)

wherein R4 is a $C_6$-$C_{20}$ alkyl group; m is a number greater than 15; Y is an alkali metal and/or alkaline earth metal, ammonium, alkylammonium or alkanolammonium.

Alkyl ether sulfates ("ether sulfates") are manufactured industrially by sulfating fatty alcohol polyglycol ethers or oxo alcohol polyglycol ethers with $SO_3$ or chlorosulfonic acid (CSA) and subsequent neutralization. Preferred examples are sulfates in the form of their sodium and/or magnesium salts of highly ethoxylated addition products of at least 16, but averaging 20 to 40 and especially 25 to 35 mole ethylene oxide (expressed as m in Formula (III)) to caproyl alcohol, capryl alcohol, 2-ethylhexyl alcohol, caprinic alcohol, lauryl alcohol, isotridecyl alcohol, myristyl alcohol, cetyl alcohol, stearyl alcohol, isostearyl alcohol, eicosyl alcohol or their technical mixtures. These result, for example, in the high pressure hydrogenation of technical methyl esters based on fats and oils, or from aldehydes from Roelen's Oxo Synthesis, as well as from the monomer fraction in the dimerization of unsaturated fatty alcohols. Technical fatty alcohols with 12 to 18 carbon atoms are preferred, such as coco, palm, palm nut or tallow fatty alcohol. In this regard, ether sulfates can have both a conventional as well as a narrowed homolog distribution. Use of ether sulfates in the form of their sodium and/or magnesium salts based on adducts of an average of 25 to 35 mole ethylene oxide to technical C12/14 or C12/18 coco fatty alcohol fractions is particularly preferred. A particularly preferred bleach co-activator is provided under the INCI name Sodium Coceth-30 sulfate and is marketed by Cognis under the trade name Disponil® FES 77 as a 31-33 wt. % conc. aqueous solution.

The bleach co-activator(s) is/are preferably used in specific quantitative ranges. Preferred agents according to the invention comprise 0.01-10 wt. %, particularly 0.1-5 wt. % of at least one toxicologically harmless bleach co-activator, based on total weight of the ready-to-use agent.

If strong lightening is desired, then it is preferred to additionally mix a blonde-dyeing preparation (C) having at least one further bleach booster with the mixture of the oxidizing agent preparation (B) and the preparation (A) comprising at least one oxidation dye precursor and at least one acylpyridinium derivative according to Formula (I).

In this regard, it can be irrelevant whether a mixture (A) and (B) is initially produced and then the blonde-dyeing preparation (C) is blended in, or whether a different sequence of blending of the individual components is utilized. Preferably, the individual preparations are blended in the shortest amount of time and the ready-to-use agent is promptly applied onto the keratin fibers.

Consequently, another embodiment of the present application is an agent for bleaching and dyeing keratinic fibers that is produced prior to application by blending at least one oxidizing agent preparation (B) having at least one oxidizing agent chosen from hydrogen peroxide and its addition products on solid carriers, at least one blond-dyeing preparation (C) having at least one bleach booster, and at least one preparation (A) having in a cosmetic carrier at least one oxidation dye precursor and at least one cationic acylpyridinium derivative according to Formula (I).

As was mentioned above, it can be advantageous to use two separate preparations (A1) comprising in a cosmetic carrier at least one oxidation dye precursor and (A2) comprising in a cosmetic carrier at least one cationic acylpyridinium derivative according to Formula (I), instead of preparation (A) comprising in a cosmetic carrier at least one oxidation dye precursor and at least one cationic acylpyridinium derivative according to Formula (I).

Consequently, another embodiment of the present application is an agent for bleaching and dyeing keratinic fibers that is produced prior to application by blending at least one oxidizing agent preparation (B) having at least one oxidizing agent chosen from hydrogen peroxide and its addition products on solid carriers, at least one blond-dyeing preparation (C) having at least one bleach booster, at least one preparation (A1) having in a cosmetic carrier at least one oxidation dye precursor, and at least preparation (A2) having in a cosmetic carrier at least one cationic acylpyridinium derivative according to Formula (I).

Here, the sequence of blending preparations (A1), (A2), (B) and (C) can be irrelevant. However, it is advantageous to first mix preparations (A1) and (A2) and then add the additional preparations, preferably as a premix of (B) and (C).

Employing only hydrogen peroxide or its addition products on organic or inorganic compounds is often insufficient for strongly lightening very dark hair. Consequently, agents according to the invention can also contain further blond-dyeing and/or bleaching agents.

Here, a combination of hydrogen peroxide and persulfates or peroxydisulfates can be used and results in an agent having an increased lightening power.

Consequently, should a consumer desire very strong blonding, it can be preferred in another embodiment for the dye to additionally contain in the agent at least one inorganic peroxy compound as blonding preparation (C) for lightening the keratinic fibers. The inorganic peroxy compound is preferably chosen from ammonium persulfate, alkali metal persulfates, ammonium peroxymonosulfate, alkali metal hydrogen peroxymonosulfates, alkali metal peroxydiphosphates and alkaline earth metal peroxides. Particularly preferred inorganic peroxy compounds as bleach boosters are ammonium peroxydisulfate, potassium peroxydisulfate, sodium peroxydisulfate, potassium hydrogen peroxymonosulfate, potassium peroxydiphosphate, magnesium peroxide and barium peroxide. Preferred inorganic peroxy compounds are peroxydisulfate salts, especially ammonium peroxydisulfate, potassium peroxydisulfate and sodium peroxydisulfate. The ready-to-use agent preferably contains peroxy disulfate salts in amounts of 0.1 to 25 wt. %, particularly 0.5 to 15 wt. %, based on total weight of the ready-to-use agent.

However, it can be advantageous for the agent to be exempt from inorganic peroxy compounds. Agents according to the invention can, however, contain an additional bleach booster instead of and/or in addition to the solid peroxy compounds.

According to the invention, carbonic acid derivatives, alkyl carbonates and alkyl carbamates, as well as silyl carbonates and silyl carbamates can be used as additional bleach boosters, compounds that under perhydrolysis conditions afford aliphatic peroxycarboxylic acids and/or substituted perbenzoic acid. The agents can preferably contain at least one compound chosen from acetic acid, lactic acid, tartaric acid, citric acid, salicylic acid and ortho-phthalic acid as an additional bleach booster. Bleach boosters used in addition to, or instead of, peroxy compounds are present in cosmetic agents according to the invention preferably in amounts of 0.05 to 10% by weight, particularly 0.2 to 5% by weight, based on total weight of the ready-to-use agent.

Although there is generally no limitation regarding formulation of blonding preparation (C), preferably preparation (C) is an anhydrous formulation.

According to the present invention, anhydrous refers to a water content, based on preparation (C), of 5 wt. % or less, especially 2 wt. % or less. Blonding preparations having less than 0.1 wt. % water can be quite particularly preferred. Preparation (C) is preferably formulated as a powder or an anhydrous paste. When the formulation is an anhydrous paste, it has proven particularly preferable when preparation (C) contains at least one non-hydroxylated fatty acid ester with a melting point of no more than 50° C., particularly no more than 30° C., and/or at least one $C_{10}$-$C_{30}$ fatty acid containing at least one additional hydroxyl group and/or a derivative thereof. Esters of non-hydroxylated $C_6$-$C_{30}$ alkyl monocarboxylic acids with $C_2$-$C_{30}$ monohydric alcohols are preferably suitable as the fatty acid ester. Monoesters of fatty acids with monohydric alcohols having 2 to 24 carbon atoms are preferred. According to the invention, isopropyl myristate, isononanoic acid $C_{16-18}$ alkyl ester, 2-ethylhexyl palmitate, stearic acid 2-ethylhexyl ester, cetyl oleate, coco fatty alcohol caprinate/-caprylate, n-butyl stearate, oleyl erucate, isopropyl palmitate, oleyl oleate, lauric acid hexyl ester, myristyl myristate, cetearyl isononanoate and oleic acid decyl ester are particularly preferred.

A preferred embodiment of the present invention is one wherein the ready-to-use agent has a pH from 7 to 11, particularly from 8 to 10.5, particularly preferably from 8.5 to 10.0. According to the present invention, pH values refer to those measured at a temperature of 22° C.

The pH is usually adjusted with pH adjustors. One skilled in cosmetics commonly uses established acidifiers and alkalizers to adjust the pH. Alkalizers that can be used for adjusting pH are typically chosen from inorganic salts, especially from alkali and alkaline earth metals, organic alkalizers, especially amines, basic amino acids and alkanolamines, and ammonia. Inventively preferred acidifiers are food acids such as citric acids, acetic acid, malic acid or tartaric acid, as well as diluted mineral acids. Particularly preferred alkanolamines are monoethanolamine and triethanolamine. The alkalizers are preferably present in amounts of 0.05 to 10 wt. %, particularly 0.5 to 5 wt. %, based on total weight of the ready-to-use agent.

As previously mentioned the agents can also be produced from two or more separately packaged preparations immediately prior to use. This allows separation of incompatible ingredients in order to avoid premature reaction. Separation into multi-component systems is particularly appropriate where incompatibilities of the ingredients are to be expected or to be feared. In these types of systems, the ready-to-use agent is produced by the user by blending the components immediately prior to use. A dyeing and/or lightening agent where the oxidation dye precursors are initially present separate from the oxidizing agent preparation is preferred.

A preferred presentation form of the agent according to the invention is a kit-of-parts having in separate containers
   at least one oxidizing agent preparation (B) having at least one oxidizing agent, and
   at least one preparation (A), wherein preparation (A) has in a cosmetic carrier at least one oxidation dye precursor as well as at least one acylpyridinium derivative according to Formula (I).

A further preferred presentation form of the agent according to the invention is a kit-of-parts that in separately prepared containers comprises
   at least one oxidizing agent preparation (B) containing at least one oxidizing agent,
   at least one preparation (A1) that in a cosmetic carrier contains at least one oxidation dye precursor, and
   at least one preparation (A2), wherein preparation (A2) contains in a cosmetic carrier at least one acylpyridinium derivative according to Formula (I).

If a particularly strong lightening effect is desired, then a further preferred presentation form of the agent is a kit-of-parts that in separately prepared containers comprises
   at least one oxidizing agent preparation (B) containing at least one oxidizing agent,
   at least one blonding preparation (C) containing at least one bleach booster, and
   at least one preparation (A), wherein preparation (A) comprises in a cosmetic carrier at least one oxidation dye precursor as well as at least one acylpyridinium derivative according to Formula (I).

Finally, a further preferred presentation form of the agent for a particularly strong lightening effect is a kit-of-parts that in separately prepared containers comprises
   at least one oxidizing agent preparation (B) containing at least one oxidizing agent, at least one blonding preparation (C) containing at least one bleach booster, at least one preparation (A1) containing in a cosmetic carrier at least one oxidation dye precursor, and at least one preparation (A2), wherein preparation (A2) comprises in a cosmetic carrier at least one acylpyridinium derivative according to Formula (I).

The multi-component kit-of-parts preferably also contains an instruction manual. Moreover, it can be preferred that an application aid such as a comb or a brush, and/or a personal protection kit such as disposable gloves, is supplied with the kit. With reference to further preferred embodiments of the multi-component kit-of-parts, the statement made concerning the agents according to the invention applies mutatis mutandis.

Mixture of preparation (A), or (A1) and (A2), with (B) or optionally of the preparation (A), or (A1) and (A2), with (B) and (C) prior to application yields an application mixture according to the invention.

The actual hair dye is advantageously produced immediately prior to application by mixing preparation (A), or (A1) and (A2), with (B) as well as optionally (C). Application temperatures can be in a range from 15 to 40° C. After a contact time of 5 to 45 minutes, the hair dye is removed from the hair by rinsing. There is no need to wash the hair with a shampoo afterwards if a strong surfactant-containing carrier (e.g., a color enhancing shampoo) was used.

Accordingly, another subject matter of the present invention is a method for dyeing and lightening human hair, wherein an agent according to the above specifications is deposited on the hair, left on the hair for a contact time of 2 to 45 minutes, preferably 5 to 20 minutes, quite particularly preferably 8 to 15 minutes, and subsequently rinsed out of the hair with water and/or washed out with a shampoo.

Another subject matter of the invention is use of an agent according to the invention for dyeing and simultaneously lightening keratin-containing fibers, especially human hair. With reference to further preferred embodiments of the methods and uses according to the invention, the statement made concerning the agents according to the invention applies mutatis mutandis.

The following examples are intended to illustrate preferred embodiments of the invention without however limiting it.

EXAMPLES

1. Synthesis Examples

1.1 Synthesis of 4-acetyl-1-methylpyridinium p-toluene sulfonate

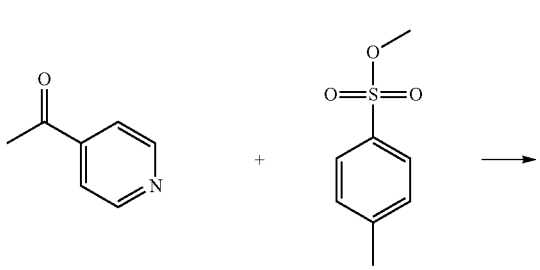

-continued

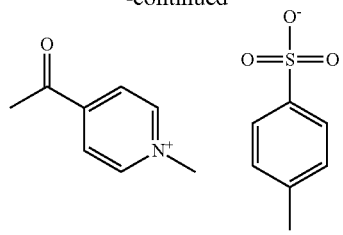

4-Acetylpyridine (30.0 g, 0.25 mol) and p-toluene sulfonic acid methyl ester (55.8 g, 0.30 mol) in 500 ml ethanol were heated under reflux for 5 hours. The solvent was removed under vacuum in a rotary evaporator and the residue was taken up in ether. After separating off the ether phase, the product slowly crystallized out. The product was dried under vacuum. Yield: 59.9 g (82.5%); $^1$H-NMR (400 MHz, DMSO-d6): [delta] [ppm]=2.26 (s, 3H); 2.72 (s, 3H); 3.39 (s, 3H); 7.11 (d, 2H); 7.49 (d, 2H); 8.42 (d, 2H); 9.20 (d, 2H); $^{13}$C-NMR (400 MHz, DMSO-d6): [delta] [ppm]=20.8; 26.4; 48.1; 124.8; 125.3; 127.7; 138.9; 145.2; 146.5; 148.3; 195.8.

2. Examples of Blonding

2.1 Production of Blonding Cream

Blonding creams were produced from the following listed ingredients:

|  | wt. % | |
| --- | --- | --- |
| Raw Material | V1 | E1 |
| Hydrenol D | 4.0 | 4.0 |
| Lorol techn. | 2.4 | 2.4 |
| Eumulgin B3 | 0.2 | 0.2 |
| Eumulgin B2 | 0.2 | 0.2 |
| Mergital CS 50 A | 0.8 | 0.8 |
| 1,2-Propane diol | 0.4 | 0.4 |
| Xanthane FN | 0.1 | 0.1 |
| Crodafos CES | 2.0 | 2.0 |
| Amphoterge K-2 | 2.0 | 2.0 |
| Merquat 281 | 3.0 | 3.0 |
| Ammonium sulfate | 2.0 | 2.0 |
| Sodium sulfate | 0.1 | 0.1 |
| L-arginine | 1.0 | 1.0 |
| p-Toluenediamine sulfate | 0.1 | 0.1 |
| Resorcinol | 0.1 | 0.1 |
| HEDP 60% | 0.2 | 0.2 |
| Sodium silicate 40/42 | 0.5 | 0.5 |
| Ammonia 25% | 10.0 | 10.0 |
| 4-Acetyl-1-methylpyridinium p-toluene sulfonate acc. 1.1 | — | 1.0 |
| Water | ad 100 | ad 100 |

2.2 Blending with the Developer Dispersion

Each blonding cream was mixed up in a ratio of 1:1 with one of the following formulated developer dispersions. The pH of the application mixture was from 9 to 10.2.

| Raw Material | wt. % |
| --- | --- |
| Sodium hydroxide 45% | 0.73 |
| Dipicolinic acid | 0.10 |
| Disodium pyrophosphate | 0.03 |

-continued

| Raw Material | wt. % |
|---|---|
| HEDP 60% | 1.5 |
| FAEOS-Na C12-14 2EO 27% | 2.0 |
| Dow Corning DB 110 A | 0.07 |
| Aculyn 33A | 2.5 |
| Hydrogen peroxide 50% | 20.00 |
| Water | ad 100 |

| | |
|---|---|
| Hydrenol ® D | INCI name: Cetearyl Alcohol (Cognis) |
| Lorol ® C12-18, techn. | INCI name: Coconut Alcohol (Cognis) |
| Eumulgin ® B3 | INCI name: Ceteareth-30 (Cognis) |
| Eumulgin ® B2 | INCI name: Ceteareth-20 (Cognis) |
| Mergital ® CS 50 | INCI name: Ceteareth-50 (Cognis) |
| Crodafos ® CES | INCI name: Cetearyl Alcohol, Dicetyl Phosphate, Ceteth-10 Phosphate (Croda) |
| Merqua ® 281 | INCI name: Polyquaternium-22 (Nalco) |
| Amphoterge ® K-2 | INCI name: Disodium Cocoamphodipropionate (Lonza) |
| Dow Corning ® 110 A | INCI name: Dimethicone (Dow Corning) |
| Aculyn ® 33A | INCI name: Acrylates Copolymer (ISP) |

For the dyeing process, strands of dark blond hair (Code Kerling 7/0), weighing ca. 0.7 g were treated with four times the amount of the premixed application mixture. After blonding the strands for 10 minutes at 32° C., they were washed with a conventional shampoo and dried with a hair dryer.

2.3 Evaluation of the Lightening and Dyeing Power

Each strand of hair was measured colorimetrically before and after the bleaching process. An L-value, a-value and b-value were determined for each measurement. The L-value represents the lightness of the dyeing (black-white axis); the greater the L-value, the lighter is the dyeing. The a-value represents the red-green axis of the system; the greater the value, the more the dyeing has shifted into the red. The b-value represents the yellow-blue axis of the system; the greater the value, the more the dyeing has shifted into the yellow.

The dL-value according to the following equation (I) was consulted as a measure for lightening power of each formulation:

$$\Delta L = L_{after} - L_{before} \qquad \text{equation (I)}$$

$L_{after}$=lightness of the strands after the dyeing process
$L_{before}$=lightness of the strands before the dyeing process Color differences were characterized by ΔE-value, calculated from the three measured values according to equation (II):

$$\Delta E = \sqrt{(\Delta L)^2 + (\Delta a)^2 + (\Delta b)^2} \qquad \text{equation (II)}$$

$\Delta a = a_{after} - a_{before}$ with $a_{after}$ = a-value after the dyeing process
$a_{before}$ = a-value before the dyeing process
$\Delta b = b_{after} - b_{before}$ with $b_{after}$ = b-value after the dyeing process
$b_{before}$ = b-value before the dyeing process A repeat determination was made for each formulation, an average value being determined from each single value. The greater the ΔL-value, the better is the lightening power of the formulation. The greater the ΔE-value, the greater is the color difference in comparison with the initial hair color.

2.4 Results of the Lightening and Dyeing Power

Lightening and Dyeing Power for Dark Blond Strains (Kerling 7/0)

| ΔL (Formulation V1) | ΔL (Formulation E1) |
|---|---|
| 3.82 | 5.68 |
| ΔE (Formulation V1) | ΔE (Formulation E1) |
| 5.80 | 8.42 |

A comparison of the colorimetric measurements demonstrates that greater ΔL-values can be obtained with formulations according to the invention. Thus, blonding powers are improved with use of these formulations and are classified as being superior compared to those of the prior art. Likewise, greater ΔE-values are obtained with formulations according to the invention than with the comparative formulations. Based on initial hair color, a greater color difference can be obtained with the agent described in this invention for an application time of only 10 minutes.

We claim:

1. Agent for dyeing and simultaneously lightening keratinic fibers comprising in a cosmetic carrier:
   at least one oxidation dye precursor, and
   at least one cationic acylpyridinium derivative according to the following Formula (I),

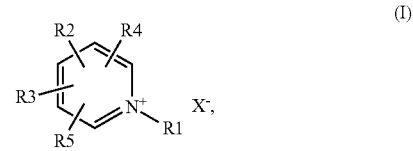

wherein
   R1 is a $C_1$-$C_6$ alkyl group, a $C_2$-$C_6$ alkenyl group, a $C_2$-$C_6$ hydroxyalkyl group, a $C_1$-$C_6$ alkoxy $C_2$-$C_6$ alkyl group, a carboxy $C_2$-$C_6$ alkyl group, an aryl $C_1$-$C_6$ alkyl group, a heteroaryl $C_1$-$C_6$ alkyl group, an aryl group or a heteroaryl group;
   R2 is an acyl group according to the formula R'C(O) in which R' is a $C_1$-$C_6$ alkyl group, a $C_2$-$C_6$ hydroxyalkyl group, a $C_1$-$C_6$ alkoxy $C_2$-$C_6$ alkyl group, a carboxy $C_1$-$C_6$ alkyl group, an aryl $C_1$-$C_6$ alkyl group, or a heteroaryl $C_1$-$C_6$ alkyl group;
   R3, R4 and R5 are, independently of one another, a hydrogen atom, a hydroxyl group, an amino group, a di-($C_1$-$C_6$ alkyl)amino group, a $C_1$-$C_6$ alkyl group, a $C_1$-$C_6$ alkoxy group, a $C_1$-$C_6$ alkoxy $C_2$-$C_6$ alkyl group, a halogen, a nitro group, a carboxy group, a nitrile group, an optionally substituted aryl group, a $C_2$-$C_6$ alkenyl group, an optionally substituted heteroaryl group; and
   $X^-$ is a physiologically acceptable anion.

2. Agent according to claim 1 wherein R1 is a $C_1$-$C_6$ alkyl group, a $C_2$-$C_6$ alkenyl group, or a $C_2$-$C_6$ hydroxyalkyl group.

3. Agent according to claim 1 wherein R2 is an acyl group having the formula R'C(O), wherein R' is a $C_1$-$C_6$ alkyl group.

4. Agent according to claim 1 wherein R2 is in the 2-position or 4-position of Formula (I).

5. Agent according to claim 1 wherein R3, R4 and R5 are hydrogen.

6. Agent according to claim 1 wherein $X^-$ is a halide ion, hydrogen sulfate, ½ sulfate, p-toluene sulfonate, benzene sulfonate, or acetate.

7. Agent according to claim 1 wherein the acylpyridinium derivative according to Formula (I) is chosen from 4-acetyl-1-methylpyridinium p-toluene sulfonate, 4-acetyl-1-methylpyridinium benzene sulfonate, 4-acetyl-1-methylpyridinium bromide, 4-acetyl-1-methylpyridinium chloride, 4-acetyl-1-methylpyridinium hydrogen sulfate, 4-acetyl-1-methylpyridinium acetate, 4-acetyl-1-allylpyridinium p-toluene sulfonate, 4-acetyl-1-allylpyridinium benzene sulfonate, 4-acetyl-1-allylpyridinium bromide, 4-acetyl-1-allylpyridinium chloride, 4-acetyl-1-allylpyridinium hydrogen sulfate, 4-acetyl-1-allylpyridinium acetate, 2-acetyl-1-methylpyridinium p-toluene sulfonate, 2-acetyl-1-methylpyridinium benzene sulfonate, 2-acetyl-1-methylpyridinium bromide, 2-acetyl-1-methylpyridinium chloride, 2-acetyl-1-methylpyridinium hydrogen sulfate, 2-acetyl-1-methylpyridinium acetate, 2-acetyl-1-allylpyridinium p-toluene sulfonate, 2-acetyl-1-allylpyridinium benzene sulfonate, 2-acetyl-1-allylpyridinium bromide, 2-acetyl-1-allylpyridinium chloride, 2-acetyl-1-allylpyridinium hydrogen sulfate or 2-acetyl-1-allylpyridinium acetate.

8. Agent according to claim 1 wherein the acylpyridinium derivative according to Formula (I) is present in an amount of 0.01 to 15 wt. %, based on total weight of the agent.

9. Method for preparing an agent according to claim 1 comprising:
providing at least two preparations in at least two separately packaged containers, wherein at least a first container comprises a dye (A) having in a cosmetic carrier at least one oxidation dye precursor as well as at least one acylpyridinium derivative according to Formula (I), and at least a second container has an oxidizing agent preparation (B) comprising at least one oxidizing agent, and
blending directly prior to use the at least two preparations, thereby producing the agent.

10. Method according to claim 9, wherein the oxidizing agent is present in an amount of 0.5 to 12 wt. %, based on total weight of the agent.

11. Method according to claim 9, wherein the oxidizing agent of preparation (B) is at least hydrogen peroxide and/or one of its solid addition products on organic or inorganic compounds.

12. Agent according to claim 1 further comprising a toxicologically harmless bleach co-activator according to Formula (II) and/or a physiologically acceptable salt thereof,

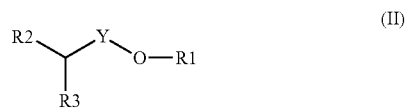

wherein
Y is a carbonyl group, a direct bond or methylene group,
R1 is hydrogen, a $C_1$-$C_4$ alkyl group, a physiologically acceptable cation or a $SO_3^-$ or a $PO_3^{2-}$ group,
R2 is an amino, a methylamino, a dimethylamino, a trimethylammonio group, phenyl, benzyl, phenoxymethyl, 1-naphthyl, 2-naphthyl, 2-, 3-, 4-toluoyl, or a R4-O—$(CH_2CH_2O)_n$ group, in which R4 is a $C_6$-$C_{20}$ alkyl group and n is a number greater than 15, and
R3 is hydrogen or an optionally branched $C_1$-$C_6$ alkyl group,
with the proviso that, when Y is a carbonyl group,
R1 is hydrogen, a $C_1$-$C_4$ alkyl group or a physiologically acceptable cation,
R2 is an amino, a methylamino, a dimethylamino or a trimethylammonio group, and
R3 is hydrogen or an optionally branched $C_1$-$C_6$ alkyl group,
with the proviso that, when Y is a direct bond,
R1 is hydrogen and
R2 is phenyl, benzyl, phenoxymethyl, 1-naphthyl, 2-naphthyl, 2-, 3- or 4-toluoyl, and
R3 is hydrogen or an optionally branched $C_1$-$C_6$ alkyl group, and
with the proviso that, when Y is a methylene group,
R1 is a $SO_3^-$ or a $PO_3^{2-}$ group,
R2 is a R4-O—$(CH_2CH_2O)_n$ group, in which R4 is a $C_6$-$C_{20}$ alkyl group and n is a number greater than 15, and
R3 is hydrogen.

13. Agent according to claim 1 having a pH of from 7 to 11.

14. Method for lightening keratinic fibers comprising applying an agent according to claim 1 onto the keratinic fibers, leaving the agent on the fibers for 5 to 45 minutes, and rinsing out the agent with water or washing out the agent with a shampoo.

* * * * *